(12) United States Patent
Palzkill et al.

(10) Patent No.: US 10,024,856 B2
(45) Date of Patent: Jul. 17, 2018

(54) IDENTIFICATION AND CHARACTERIZATION OF A PEPTIDE AFFINITY REAGENT FOR THE DETECTION OF NOROVIRUSES IN CLINICAL SAMPLES

(71) Applicant: Baylor College of Medicine, Houston, TX (US)

(72) Inventors: Timothy Gerald Palzkill, Houston, TX (US); Mary K. Estes, Houston, TX (US); Robert Legare Atmar, Houston, TX (US); Jennifer Dawn Rogers, Houston, TX (US); Nadim Jose Ajami, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 22 days.

(21) Appl. No.: 14/777,714

(22) PCT Filed: Mar. 21, 2014

(86) PCT No.: PCT/US2014/031437
§ 371 (c)(1),
(2) Date: Sep. 16, 2015

(87) PCT Pub. No.: WO2014/153507
PCT Pub. Date: Sep. 25, 2014

(65) Prior Publication Data
US 2016/0061835 A1   Mar. 3, 2016

Related U.S. Application Data

(60) Provisional application No. 61/803,825, filed on Mar. 21, 2013.

(51) Int. Cl.
| | | |
|---|---|---|
| A61K 38/00 | (2006.01) | |
| G01N 33/569 | (2006.01) | |
| C07K 7/08 | (2006.01) | |

(52) U.S. Cl.
CPC ......... *G01N 33/56983* (2013.01); *C07K 7/08* (2013.01); *A61K 38/00* (2013.01); *G01N 2333/08* (2013.01); *G01N 2469/10* (2013.01)

(58) Field of Classification Search
None
See application file for complete search history.

(56) References Cited

U.S. PATENT DOCUMENTS

| | | | | |
|---|---|---|---|---|
| 6,764,851 B2 * | 7/2004 | Nikolau | ............... | C12N 9/0008 435/320.1 |
| 9,029,636 B2 * | 5/2015 | Wu | ...................... | C07K 14/415 435/419 |
| 2007/0044171 A1 * | 2/2007 | Kovalic | ............... | C07K 14/415 800/278 |
| 2011/0020786 A1 | 1/2011 | Palzkill et al. | | |

FOREIGN PATENT DOCUMENTS

| | | |
|---|---|---|
| DE | 102011118031 A1 | 12/2012 |
| WO | 2012134416 A2 | 10/2012 |

OTHER PUBLICATIONS

Sano et al. (Journal of Applied Microbiology 109, 1923-1928, 2010).*
Sano et al. "Norovirus-binding proteins recovered from activated sludge micro-organisms with an affinity to a noroviral capsid peptide," Journal of Applied Microbiology, Dec. 1, 2010 (Dec. 1, 2010), vol. 109, Iss. 6, pp. 1923-1928.
Rogers et al. "Identification and Characterization of a Peptide Affinity Reagent for Detection of Noroviruses in Clinical Samples," Journal of Clinical Microbiology, vol. 51, No. 6, pp. 1803-1808.

* cited by examiner

*Primary Examiner* — Jennifer Pitrak McDonald
*Assistant Examiner* — Sergio Coffa
(74) *Attorney, Agent, or Firm* — Norton Rose Fulbright US LLP

(57) ABSTRACT

Embodiments of the disclosure include methods and/or compositions for the detection of viral infection, including at least *Norovirus* infection. In particular embodiments, there are methods and/or compositions employing particular peptides and/or phage useful for detecting *Norovirus* in a sample. The sample may be from an environment or from an individual. The individual may be a mammal, including a human, cow, horse, dog, cat, pig, and so forth. Certain exemplary peptides and phage that express the peptides are identified as useful for binding to *Norovirus*. Such peptides and phage are provided to one or more samples in order to identify whether or not *Norovirus* is present in the sample.

5 Claims, 3 Drawing Sheets

SEQUENCE LISTING

<160> NUMBER OF SEQ ID NOS: 23

<210> SEQ ID NO 1
<211> LENGTH: 12
<212> TYPE: PRT
<213> ORGANISM: Artificial Sequence
<220> FEATURE:

```
<223> OTHER INFORMATION: Synthetic Peptide

<400> SEQUENCE: 1

Leu Pro Ser Trp Tyr Leu Ala Tyr Gln Lys Ile Ile
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 2

Leu Pro Ser Trp Tyr Leu
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 3

Leu Asp Tyr Arg Ser Trp Ser Pro Tyr Ala Thr Ser
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 4

Leu Asp Tyr Ala Ser Trp Ser Pro Ala Ala Thr Ser
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 5

Ile Gln Tyr Arg Ser Trp Ile Pro Phe Ser Tyr Pro
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 6

Ile Gln Tyr Ala Ser Trp Ile Pro Phe Ser Tyr Pro
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide
```

```
<400> SEQUENCE: 7

Trp Ser His Pro Gln Phe Glu Lys
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 8

Met Ala Ser Met Thr Gly Gly Gln Gln Met Gly
1               5                   10

<210> SEQ ID NO 9
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 9

Tyr Arg Ser Trp
1

<210> SEQ ID NO 10
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 10

Ala Gly Glu Leu Ser Pro Asn Arg Ser Ala Phe Leu
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 11

Gln Ile Pro Pro Arg Pro Pro Leu Leu Thr Thr Leu
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 12

His Asn Val Thr Trp Ala Ala Leu Met Ala Asn Val
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic Peptide
```

```
<400> SEQUENCE: 13

Ser Tyr Asn Thr Leu Thr Gln Ile Ala Lys Ile Arg
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 14

Asn Ser Thr Asn Pro His Glu Ser Arg Pro Thr Ser
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 15

Leu Asp Tyr Arg Ser Trp Ala Pro Tyr Ala Thr Ser
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 16

Phe Arg Ser Tyr Glu Ser Pro Asn Phe Arg Pro Pro
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 17

Tyr Arg Ser Phe Asp Pro Trp Tyr Pro Pro Val His
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 18

Leu Thr Gln Gln Arg Ser Trp Ser Pro Tyr Met Pro
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 19
```

```
Thr His Gln Asn Arg Gln Thr Ala Asp Ile Pro Ser
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 20

Leu Ser Ile Arg Ser Tyr Thr Ser Pro Gln Trp Gln
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 21

Ile Ser Trp Ala Asp Trp Thr Gln Arg Trp Arg Trp
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 22

Ala Leu Pro Thr Phe Gly Val Ile Ser Pro Phe Ser
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 23

Ser His Val Ser Lys Leu Val Tyr Gln Ser Gln Ser
1               5                   10
```

IDENTIFICATION AND CHARACTERIZATION OF A PEPTIDE AFFINITY REAGENT FOR THE DETECTION OF NOROVIRUSES IN CLINICAL SAMPLES

CROSS-REFERENCE TO RELATED APPLICATIONS

This application is a national phase application under 35 U.S.C. § 371 that claims priority to International Application No. PCT/US2014/031437 filed Mar. 21, 2014, which claims the benefit of priority to U.S. Provisional Patent Application Ser. No. 61/803,825, filed on Mar. 21, 2013, all of which are incorporated by reference herein in their entirety.

STATEMENT REGARDING FEDERALLY SPONSORED RESEARCH OR DEVELOPMENT

This invention was made with government support under Public Health Service Grants NIH P01 AI057788; NIH P30DK56338; Agriculture and Food Research Initiative Competitive Grant 2011-68003-30395 from the USDA National Institute of Food and Agriculture and a training fellowship from the Keck Center of the Gulf Coast Consortia, on Pharmacological Sciences Training Program, National Institute of General Medical Sciences (NIGMS) T32GM089657. The Government of the United States of America has certain rights in the invention.

TECHNICAL FIELD

The present disclosure encompasses at least the fields of immunology, virology, cell biology, molecular biology, and medicine.

BACKGROUND

Human *norovirus* (NoV) causes an estimated 21 million cases of gastroenteritis in the United States each year (Scallan, et al., 2011). NoVs are members of the family Caliciviridae and contain a single stranded, positive sense RNA genome. NoVs are classified into five genogroups (GI-GV) and further subdivided into genotypes based on the capsid sequence (Zheng, et al., 2006; Kroneman, et al., 2011). Most human NoVs fall within the GI and GII genogroups. *Norwalk* virus (NV), genotype GI.1, was the first NoV isolated and is considered the prototype virus of the genus; nevertheless, genotype GII.4 NoVs are currently the most frequently detected in humans (Glass, et al., 2009). NoV infection is generally self-limiting in healthy adults, requiring only rehydration and supportive therapy; however, illness can be severe and even fatal in the elderly and young children (Glass, et al., 2009; Trivedi, et al., 2012). Furthermore, infection can be chronic in immunocompromised patients, lasting years and mimicking the symptoms of transplant rejection (Kaufmann, et al., 2005; Bok & Green, 2012).

NoV's low infectious dose, resistance to many common sterilization procedures, and ease of transmission make epidemic outbreaks common and difficult to control, particularly in semi-closed environments such as schools, nursing homes, hospitals, cruise ships, and military settings (Glass, et al., 2009; Hutson, et al., 2004). NoV has been shown to be the cause of the majority of nonbacterial gastroenteritis epidemics in the United States, resulting in a huge economic burden, particularly in healthcare settings, when considering the cost of lost revenue from closures to new admissions, staff absences, and cleaning expenses (Scallan, et al., 2011; Fankhauser, et al., 1998; Hoffmann, et al., 2012; Johnston, et al., 2007). The total annual cost of healthcare and lost productivity due to foodborne illness caused by *norovirus* in the USA is estimated to be $2 billion (Hoffman, et al., 2012).

In order to manage severe and chronic NoV infections and effectively control epidemic outbreaks, rapid diagnosis is crucial. In fact, it has been observed that outbreaks were contained an average of 6 days sooner (7.9 vs 15.4 days) when diagnosis was made within three days rather than four or more days after the first case, making a huge difference in the impact of the outbreak (Lopman, et al., 2004). Only one immunoassay, the RIDASCREEN *Norovirus* ELISA ($3^{rd}$ generation), is currently available for NoV diagnosis in the USA. However, this assay is currently approved for use only in the diagnosis of outbreaks because it lacks sensitivity. Moreover, negative results are unreliable as the sensitivity is highly dependent on the genotype associated with the outbreak (Parker, et al., 2005; Atmar, et al., 2001; Ambert-Balay & Pothier, 2012; Kirby, et al., 2010).

Phage display is a powerful technique for rapidly screening large-scale libraries for novel substrates (Sidhu, et al., 2003). Phage display employs random peptide sequences as fusions to geneIII protein, which is a solvent accessible capsid protein present in five copies on one end of the phage coat (Samoylova, et al., 2012). This allows biopanning in which the phage displaying peptide are allowed to interact with the chosen target, non-interacting phage are washed away, and specifically bound phage are eluted from the target by low pH. Several rounds of biopanning enrich for peptide sequences that interact with the target (Rakonjac, et al., 2011). The advantage of phage display relies on the presence of the genetic material for these peptides within the phage chromosome, linking the genotype and phenotype for easy determination of the sequence of the binding peptide (Paschke, 2003). This method has been used previously to isolate peptide-displaying phage that are useful diagnostic substrates for other bacterial and viral pathogens such as Mycobacterium avium and, more recently, hepatitis B virus (Monjezi, et al., 2012; Schofield, et al., 2012; Stratmann, et al., 2002).

The present disclosure provides a solution for a long-felt need in the art for detection of *Norovirus*.

BRIEF SUMMARY

Embodiments of the disclosure include methods and/or compositions for the detection of viral infection, including at least *Norovirus* infection. In particular embodiments, there are methods and/or compositions employing particular peptides and/or phage useful for detecting *Norovirus* in a sample. The sample may be from an environment or from an individual. The individual may be a mammal, including a human, cow, horse, dog, cat, pig, and so forth.

Certain exemplary peptides and phage that express the peptides are identified as useful for binding to *Norovirus*. Such peptides and phage are provided to one or more samples in order to identify whether or not *Norovirus* is present in the sample. The sample may come from an individual suspected of having *Norovirus* infection (such as, the individual exhibiting one or more symptoms of *Norovirus* infection) or the sample may come from an individual suspected of being exposed to *Norovirus*, such as an individual that came into contact with an individual known to have *Norovirus* and/or having been in an environment suspected of having *Norovirus* (including pathogenic levels of *Norovirus*) or known to have *Norovirus* (including pathogenic levels of *Norovirus*).

Particular embodiments of the present disclosure provide phage display methods to identify peptides that bind to *Norovirus*, including at least *Norovirus* virus-like particle (VLP) domains (NV-VLPs). In specific embodiments, an exemplary peptide-displaying phage was isolated that interacted with NV-VLPs specifically and with high sensitivity, and it was further shown to be useful in detecting *Noroviruses* (NoVs) in samples, such as clinical stool samples. This phage was used for virus detection in an ELISA and the phage and/or the free peptide are useful for sensitive and rapid assay formats.

In one embodiment, there is a composition comprising one or both of a peptide comprising a sequence selected from the group consisting of the sequences in Table 1, or a functionally active variant thereof; and a phage that encodes the peptide or the variant. In specific embodiments, the peptide is no more than about 50 amino acids in length. In a particular embodiment, the functionally active variant comprises one, two, or three or more alterations in SEQ ID NO:1. In specific embodiments, the alterations are conservative amino acid substitutions. In a certain aspect, the functionally active variant comprises sequence that is 80%, 85%, 90%, 95%, 97%, 98%, or 99% identical to the peptide of which it is a variant. In some cases, the peptide is labeled, such as fluorescent, radioactive, or colored.

In some embodiments, there is a composition comprising an antibody that recognizes a composition of the disclosure.

In one embodiment, there is a method of identifying *Norovirus* in a sample, comprising the step of subjecting the sample to the composition of the disclosure. In specific embodiments, the subjecting step comprises binding of the peptide to the *Norovirus* to produce a peptide/*Norovirus* complex. In some embodiments, the method further comprises the step of subjecting the complex to a detectable antibody that recognizes the peptide. In specific embodiments, the peptide is labeled. In particular aspects, the subjecting step comprises binding of the phage to the *Norovirus* to produce a phage/*Norovirus* complex. In some embodiments, the method further comprises the step of subjecting the complex to a detectable antibody that recognizes the phage. In specific embodiments, the phage is labeled. Some methods further comprise the step of obtaining a sample. In certain cases, some methods further comprise the step of providing a therapy to the individual Samples for methods of the disclosure may be environmental samples, such as from a medical facility, hotel, school, airport, airplane, train, boat, cruise ship, sports facility, grocery store, long-term care facility, camp, prison, dormitory, water source, a food, child day care, or adult day care. In some embodiments, the sample is from an individual and may be a stool sample or vomitus sample.

In one embodiment, there is a kit comprising a composition of the disclosure.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION

Figure 1:
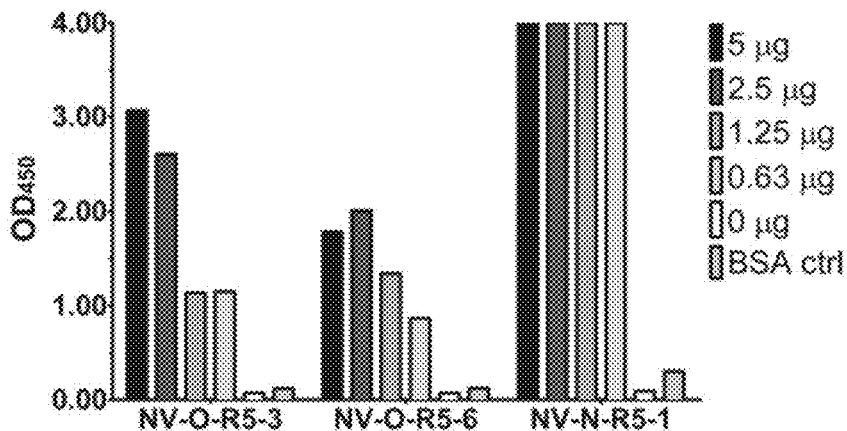
FIG. 1—Phage binding to NV-VLP. NV-VLP (5, 2.5, 1.25, 0.63 µg) or 5 µg of unrelated protein BSA was immobilized and binding of each phage, indicated on the X-axis, was detected by M13 phage antibody. $OD_{450}$ signal is indicated on the Y-axis.

As used herein, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

I. *Norovirus* and General Methods of Detection

*Noroviruses* are the most common cause of viral gastroenteritis in humans, affecting people of all ages. The present disclosure concerns detection of *Norovirus*, which is a genus (in the Caliciviridae family) of single-stranded RNA, non-enveloped viruses. The genus includes the single species called *Norwalk* virus of which the known viruses are all considered to be variant strains. For example, serotypes, strains and isolates include *Norwalk* virus; Hawaii virus; Snow Mountain virus; Mexico virus; Desert Shield virus; Southampton virus; Lordsdale virus; and Wilkinson virus. *Noroviruses* can genetically be classified into five different genogroups (GI, GII, GIII, GIV, and GV), which can be further divided into different genetic clusters or genotypes. *Noroviruses* commonly isolated in cases of acute gastroenteritis belong to two genogroups: genogroup I (GI) includes *Norwalk* virus, Desert Shield virus and Southampton virus; and II (GII), which includes Bristol virus, Lordsdale virus, Toronto virus, Mexico virus, Hawaii virus and Snow Mountain virus. The present disclosure provides for the detection of a *Norovirus* of any strain, serotype, or isolate, and the virus may be from any genogroup. In specific embodiments, a peptide herein detects GI.1 *Norovirus*.

Symptoms from *Norovirus* infection include one or more of nausea, forceful vomiting, watery diarrhea, and abdominal pain, loss of taste, lethargy, weakness, muscle aches, headache, and low-grade fever. The viruses are transmitted by fecally contaminated food or water; by person-to-person contact; and via aerosolization of the virus and subsequent contamination of surfaces. Names other than viral gastroenteritis for illnesses caused by *noroviruses* include "winter vomiting disease", "winter vomiting bug", "viral gastroenteritis", and "acute nonbacterial gastroenteritis".

In certain embodiments, there is a method of detecting *Noroviruses* in an individual having or suspected of having *Norovirus* infection, comprising the step of obtaining a sample from the individual and subjecting the sample to a peptide or phage as described herein. In specific embodiments, the peptide is labeled or an antibody that binds to the peptide is labeled.

In certain embodiments, there is a method of detecting *Norovirus* in an environment having or suspected of having *Norovirus* infection, comprising the step of obtaining a sample from the environment and subjecting the sample to a peptide or phage of the disclosure. In a specific embodiment, the peptide is labeled or an antibody that binds the peptide is labeled.

In certain embodiments, there is a method of testing for *Norovirus* infection in an individual suspected of having a *Norovirus* infection or having been exposed to *Norovirus*, comprising the steps of obtaining a stool sample from the individual, wherein the individual has a symptom of *Norovirus* infection (such as nausea, abdominal pain, abdominal cramps, and/or diarrhea); and subjecting the sample to a peptide or phage of the disclosure. In a specific embodiment, the peptide is labeled or an antibody that binds the peptide is labeled.

In specific embodiments, there is a method of testing for *Norovirus* infection in an environment suspected of having *Norovirus* or having been exposed to *Norovirus*, comprising the steps of obtaining a sample from the environment; and subjecting the sample to a peptide or phage of the disclosure. In a specific embodiment, the peptide is labeled or an antibody that binds the peptide is labeled.

In some embodiments of the invention, there is an expression construct that encodes a peptide sequence selected from the group consisting of the peptides of Table 1.

In particular embodiments of the invention, there is an isolated cell housing an expression construct that encodes a peptide sequence selected from the group consisting of the peptides in Table 1. In specific embodiments, the cell is an *E. coli*, yeast, mammalian, or insect cell, for example.

II. *Norovirus*-Binding Peptides

Embodiments of the disclosure concern peptides that have activity of binding to *Norovirus*. The peptides may bind to any part of the virus, including VP1 or VP2, for example. The VP1 inner shell domain or outer protruding domain (P-domain, which is further subdivided into the P1 subdomain and the outermost, surface exposed, P2 subdomain) may be able to be bound by one or more of the peptides of the disclosure.

In particular embodiments, one or more peptides as described in Table 1 is used for detection of *Norovirus*; combinations of peptides may be used, in certain cases. The peptides may be labeled with a detectable label, such as one that produces a fluorescence signal, colorimetric signal, radioactive signal, and so forth.

Peptide compositions may be made by any technique known to those of skill in the art, including the expression through standard molecular biological techniques, the isolation of peptide compounds from natural sources, or the chemical synthesis of peptide materials.

In some embodiments, peptides of the disclosure comprise the specific sequences in Table 1 but also further comprise additional amino acids. The additional amino acids may be on the N-terminal end of the peptide, the C-terminal end of the peptide or both. The length of the peptide may be the original 12-mers of the sequences of Table 1, although they could comprise 1, 2, 3, 4, 5, 6, 7, 8, 9, 10, or more additional amino acids. In some cases, the length of the peptide could be up to about 50 amino acids in length (such as with chemical synthesis). However, if produced by a gene fusion or expressed in *E. coli*, the length could be much longer, i.e., protein-sized, about 200-300 amino acids.

Functionally active variants of the peptides in Table 1 may be utilized to detect *Norovirus*. As used herein, the term "functionally active" refers to variant peptides that are able to detect any *Norovirus* of any kind. The variants may comprise one or more altered amino acids compared to a sequence of a peptide of Table 1. For example, there may be a substituted amino acid compared to a sequence of a peptide of Table 1, such as a conservative or even a non-conservative substitution. In addition, non-natural amino acids could be substituted by chemical synthesis.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within ±2 is preferred, those which are within ±1 are particularly preferred, and/or those within ±0.5 are even more particularly preferred.

It also is understood in the art that the substitution of like amino acids can be made effectively on the basis of hydrophilicity, particularly where the biological functional equivalent protein and/or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its immunogenicity and/or antigenicity, i.e., with a biological property of the protein.

Alterations to the peptides of the disclosure may include the twenty "natural" amino acids, and post-translational modifications thereof. However, in vitro peptide synthesis permits the use of modified and/or unusual amino acids. Exemplary, but not limiting, modified and/or unusual amino acids include the following: 2-Aminoadipic acid; 3-Aminoadipic acid; β-alanine, β-Amino-propionic acid; 2-Aminobutyric acid; 4-Aminobutyric acid, piperidinic acid; 6-Aminocaproic acid; 2-Aminoheptanoic acid; 2-Aminoisobutyric acid; 3-Aminoisobutyric acid; 2-Aminopimelic acid; 2,4-Diaminobutyric acid; Desmosine; 2,2'-Diaminopimelic acid; 2,3-Diaminopropionic acid; N-Ethylglycine; N Ethylasparagine; Hydroxylysine; allo Hydroxylysine; 3 Hydroxyproline; 4 Hydroxyproline; Isodesmosine; allo Isoleucine; N Methylglycine, sarcosine; N Methylisoleucine; 6 N Methyllysine; N Methylvaline; Norvaline; Norleucine; and Ornithine.

A peptide of the disclosure could also be produced as a cyclic peptide by chemical synthesis, in some embodiments.

III. *Norovirus*-Binding Phage

The phage displaying the *Norovirus*-binding peptide can be used in an enzyme-linked immunoabsorbant assay (ELISA) format for detection of *norovirus* from patient samples. For this purpose, the wells of a microtiter plate are coated with an antibody that binds *Norovirus*. The patient sample, commonly a 10% dilution of stool sample, is added to the wells and *Norovirus* is captured. The wells are washed with buffer and the phage is added to the well and allowed to bind. Unbound material is washed away and the bound phage is detected with a commercially available antibody linked to either a fluorescent molecule or horseradish peroxidase which produces a signal upon addition of substrate. Alternatively, the stool sample could be coated directly into microtiter wells and detected with the phage and anti-phage antibody. Also, in principle, the phage could be labeled with a fluorescent molecule and bound phage detected without an anti-phage antibody.

Detection of *Norovirus* with a peptide would entail similar steps only using a chemically synthesized peptide or a biologically produced fusion of a peptide to a carrier protein. The synthesized peptide could contain biotin for detection with streptavidin conjugated to an enzyme or fluorescent molecule. Alternatively, the peptide could be synthesized with an fluorescent label incorporated in the peptide such as a fluorescein tag. In addition, the peptide could be synthesized in the form of a dendrimer. A dendrimer consists of multiple copies of the peptide linked covalently to a core scaffold. Usually these consist of 8 or 16 linked peptides but more are possible. The advantage of the dendrimer is multi-point attachment to the target virus, which leads to higher affinity. The dendrimer can be labeled as described for the peptide.

IV. Detection Methods

Embodiments of the disclosure concern detection of *Norovirus* using one or more types of reagents that are able to bind to *Norovirus*. In particular embodiments, *Norovirus* virus-like particles are detected in research purposes with peptides or phage of the disclosure. The detection may be of the peptide, the phage, or a complex between the respective peptide or phage and the *Norovirus*. In particular embodiments, the peptide or phage is labeled such that its location, including a location attached to a *Norovirus* in a sample, may be identified. The peptide or phage may be directly labeled.

In particular embodiments, an entity other than the respective phage or peptide is employed in detection methods. For example, the entity may be able to bind to the unlabeled peptide or unlabeled phage, such as an antibody or another peptide that binds phage. The antibody itself (which may be referred to as a first antibody) may be labeled, a second antibody that binds the first antibody may be labeled.

In specific embodiments, an antibody is employed to detect a phage or peptide that binds to a *Norovirus*. Such immunobinding methods include obtaining a sample suspected of having *Norovirus* and contacting the sample with a phage or peptide that binds the *Norovirus*, followed by providing an antibody that binds the peptide or phage under conditions effective to allow the formation of immunocomplexes.

In terms of antigen detection, the biological sample analyzed may be any sample that is suspected of containing *Norovirus*, such as, for example, a stool specimen, a tissue section or specimen.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with the respective peptide or phage. After this time, the sample-peptide/phage-antibody composition will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first step labeled (such as biotinylated) monoclonal or polyclonal antibody is used to detect the target antigen(s), and a second step antibody is then used to detect the label (for example, biotin) attached to the complexed biotin. In that method the sample to be tested and that has already been exposed to the peptide or phage is first incubated in a solution containing the first step antibody. If the target phage or peptide is present, some of the antibody binds to the phage or peptide to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used, for example.

In one exemplary ELISA, the antibodies of the disclosure are immobilized onto a selected surface (referred to as "capture" antibodies) exhibiting protein affinity, such as a well in a polystyrene microtiter plate. Then, a test composition suspected of containing the respective phage or peptide bound to the *Norovirus*, such as from a clinical sample, is added to the wells. After binding and/or washing to remove non-specifically bound immune complexes, the bound antigen may be detected. Detection is generally achieved by the addition of a detection antibody that is linked to a detectable label. This type of ELISA is a simple "sandwich ELISA". In certain embodiments of the invention, the antibodies may be capture or detection antibodies.

In certain embodiments, there are variations in detection of the second antibody. In certain aspects, binding of the second antibody to the captured phage/*Norovirus* complex or peptide/*Norovirus* complex is the detection event. The second antibody could be directly labeled with an indicator enzyme or fluorescent label or it could be detected with another antibody, for example.

Other ELISAs may be used, such as involving the use of antibody competition in the detection. Irrespective of the format employed, ELISAs have certain features in common, such as coating, incubating and binding, washing to remove non-specifically bound species, and detecting the bound immune complexes.

After incubation with the labeled antibody, and subsequent to washing to remove unbound material, the amount of label may be quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

V. Kits of the Disclosure

Any of the compositions described herein may be comprised in a kit. In a non-limiting example, one or more peptides and/or phage may be comprised in a kit, including peptides that comprise a sequence listed in Table 1. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful.

However, the components of the kit may be provided as dried powder(s). When reagents and/or components are provided as a dry powder, the powder can be reconstituted by the addition of a suitable solvent. It is envisioned that the solvent may also be provided in another container means.

The kits may also comprise a second container means for containing a sterile, pharmaceutically acceptable buffer and/or other diluent.

In particular embodiments, there are one or more apparatuses in the kit suitable for extracting one or more samples from an individual. The apparatus may be a syringe, swab, scalpel, and so forth.

Embodiments of the kit may include one or more therapies for *Norovirus* infection or one or more symptoms thereof, such as an intravenous fluid bag.

EXAMPLES

The following examples are included to demonstrate preferred embodiments of the disclosure. It should be appreciated by those of skill in the art that the techniques disclosed in the examples that follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Material and Methods

VLP production—*Norwalk* virus (NV) VLPs were expressed and purified as reported previously (Hale, et al., 1999). Briefly, the VP1 and VP2 capsid proteins were expressed from a baculovirus vector in Sf9 insect cells and purified using a cesium chloride gradient. Proper VLP structure was confirmed by electron microscopy and the VLPs were stored at 4° C.

Phage biopanning—Five micrograms of NV-VLP suspended in 100 µl of phosphate-buffered saline (PBS) buffer was immobilized in immunotubes (Nalgene) overnight at 4° C. After washing twice with 1 mL PBS, the tubes were blocked with 2% non-fat dry milk in PBS, shaking gently at room temperature for 2 hours. Tubes were washed three more times with PBS. The Ph.D-12 phage display library (New England Biolabs) was diluted to $10^{11}$ pfu/ml in PBS and incubated in VLP-coated tubes for two hours at room temperature, shaking gently. Subsequent rounds of panning were performed with the same amount of amplified phage from the previous panning round. Tubes were washed 10-30 times (increasing washes in each subsequent round) with 1 mL PBS-T (1×PBS, 0.05% Tween-20). Phages that interact with the VLP target were eluted with 1 mL of elution buffer (0.2M glycine pH2.2, 1 mg/mL BSA) and neutralized after 10 minutes with 1 M Tris, pH 9.2.

For phage titration, eluted phage were diluted 10-30-fold in PBS and 10 µl of diluted phage were incubated with 200 µl of mid-log phase *E. coli* $ER_{2738}$ cells at room temperature for 10 minutes before being spread in top agar on LB plates containing 0.2 mM IPTG and 0.1 mM X-gal. Plates were incubated overnight at 37° C. and the blue plaques were counted. Also, white plaques were counted and considered an indication of contamination in the stock.

Eluted phage were amplified by inoculating 20 mL of mid-log *E. coli* $ER_{2738}$ cells with 250 µl of eluted phage. Infected cells were grown with shaking at 37° for 3-5 hours, followed by centrifugation at 3000×g for 10 min to remove cells. Supernatant was transferred to a fresh tube and 5 mL of 20% polyethylene glycol-8000, 2.5M NaCl was added and mixed well. Phage were allowed to precipitate for at least 3 hours and pelleted by centrifugation at 3000×g for 30 minutes. Phage pellets were suspended in 1 mL of PBS. Centrifugation at 13,000×g for 10 minutes removed cellular debris and the phage were titered at dilutions of $10^8$-$10^{10}$ using methods described above.

Sequencing of phage peptides—The solution containing eluted phages was used to infect *E. coli* and individual phage plaques were obtained as described for phage titer determinations. For phage amplification, 8-12 individual blue phage plaques were picked and used to inoculate 1 mL of mid-log *E. coli* $ER_{2738}$ cells in a deep-well 96-well plate. Infected cultures were grown at 37° C. with shaking for 3-5 hours. Cells were removed by centrifugation at 3000×g for 15 minutes and the supernatant containing phage was transferred to a fresh 96-well plate.

PCR amplification targeted the region containing the library sequence and was performed with 5 µl of phage supernatant as the template. PCR products were then sequenced to determine the nucleotide sequence and thereby determine the sequence of the displayed peptide (Lonestar Labs, Houston, Tex.).

Enzyme-linked immunosorbent assay (ELISA)—Initial ELISA experiments were performed by directly coating 0-5 µg of NV-VLP in 96-well polystyrene plates overnight. Wells were blocked with 2% milk in PBS for 2 hours at room temperature. After washing 3 times with PBS, $1\times10^{11}$ phage in 1% milk-PBS were added and incubated at room temperature with gentle rocking for 2 hours. Plates were washed 10 times with PBS-T. HRP-conjugated M13-antibody (Pharmacia Biotech) was diluted 1:5000 in 1% milk PBS and 100 µl was added to each well and incubated at room temperature for 45 minutes. After washing with PBS-T, HRP substrate, 3,3',5'-tetramethylbenzidine (TMB)(KPL) was added to each well. Development was allowed to proceed for 10-20 minutes and stopped with 1M $H_3PO_4$ (KPL). Optical density was measured at 450 nm on a Tecan infinite M200pro plate reader.

Capture ELISAs were performed by adsorbing rabbit polyclonal *Norwalk* virus antibody diluted 1:5000 in the wells of a 96-well polystyrene plate overnight. After blocking wells with 10% milk for 1 hour at room temperature, 0-100 ng of VLP was diluted in PBS and incubated in antibody-coated wells for 2 hours at room temperature for capture. The wells were washed 3 times with PBS-T and $1\times10^{10}$ pfu/ml NV-N-R5-1 phage, 1:2500 dilution of polyclonal antibody, or 1:500 dilution of mAb 3912 was prepared in 2% milk and 100 µl was added to each well. The plate was incubated at room temperature for 2 hours and then washed 5 times with PBS-T. Anti-rabbit secondary antibody, anti-mouse secondary antibody, or M13 phage antibody was used for detection as described above. A negative control either lacking primary antibody or with non-peptide displaying M13 phage yielded background absorbance and these values were subtracted from each well. To determine the limit of detection for NV-N-R5-1 phage and antibodies, each sample was analyzed in triplicate and the cutoff for positive signal was determined by calculating three standard deviations above the [VLP]=0 background.

Stool samples were collected from persons infected with NV, a GI.1 virus, as described previously (Atmar, et al., 2008) and stored at −80° C. Samples were weighed and suspended in PBS to create a 10-20% w/v solution. The solution was vortexed thoroughly and then clarified by centrifugation at 8000×g for 10 min. Stool samples for ELISA were used at 10% or diluted to stated concentrations in PBS. Samples had been previously characterized by RT-PCR and were further determined to be positive or negative for NV capsid antigen by antigen ELISA.

SPOT synthesis—Peptides sequences were synthesized on nitrocellulose membranes by automated SPOT synthesis on a Multipep RS (Intavis, Bergisch Gladbach, Germany) as described previously (Frank & Overwin, 1996). After synthesis, were soaked in methanol for 10 minutes, followed by two 10-minute washes in PBS before being blocked with Superblock Blocking Buffer (Thermo Scientific) overnight at 4° C. with gentle rocking. The following day, the membrane was washed three times for 10 minutes each with were chosen for sequencing of the 5'-end of geneIII encoding the library peptides. Three phage clones encoding sequences that occurred most commonly were chosen to move forward to study VLP-binding characteristics (Table 1). For this purpose, each of the three chosen phage clones was used to infect *E. coli* to amplify the phage stocks for binding experiments. All three of the chosen sequences contain an SW motif and two sequences, phage clones NV-O-R5-3 and NV-O-R5-6, contain an extended motif, YRSW [SEQ ID NO. 9].

TABLE 1

Amino acid sequences of phage clones identified by biopanning.

| | ROUND 3 | ROUND 4 | ROUND 5 | PHAGE CLONE |
|---|---|---|---|---|
| Experiment 1 | LDYRSWSPYATS (3X) [SEQ ID NO. 3] | LDYRSWAPYATS (5X) [SEQ ID NO. 15] | LDYRSWAPYATS (4X) [SEQ ID NO. 15] | NV-O-R5-3 |
| | AGELSPNRSAFL [SEQ ID NO. 10] | IQYRSWIPFSYP (2X) [SEQ ID NO. 5] | IQYRSWIPFSYP [SEQ ID NO. 5] | NV-O-R5-36 |
| | QIPPRPPLLTTL [SEQ ID NO. 11] | FRSYESPNFRPP (2X) [SEQ ID NO. 16] | LSIRSYTSPQWQ (2X) [SEQ ID NO. 20] | |
| | HNVTWAALMANV [SEQ ID NO. 12] | YRSFDPWYPPVH [SEQ ID NO. 17] | YRSFDPWYPPVH (2X) [SEQ ID NO. 17] | |
| | SYNTLTQIAKIR [SEQ ID NO. 13] | LTQQRSWSPYMP [SEQ ID NO. 18] | | |
| | NSTNPHESRPTS [SEQ ID NO. 14] | THQNRQTADIPS [SEQ ID NO. 19] | | |
| Experiment 2 | LPSWYLAYQKII (9X) [SEQ ID NO. 1] | LPSWYLAYQKII (10X) [SEQ ID NO. 1] | LPSWYLAYQKII (11X) [SEQ ID NO. 1] | NV-N-R5-1 |
| | ISWADWTQRWRW (2X) [SEQ ID NO. 21] | SHVSKLVYQSQS [SEQ ID NO. 23] | | |
| | ALPTFGVISPFS [SEQ ID NO. 22] | | | |

Note:
The frequency of sequences that appeared multiple times is indicated in parenthesis.

SPOT wash buffer (PBS-T, 1% BSA). NV-VLP was diluted to a concentration of 1 µg/ml in SPOT wash buffer and incubated with the membrane for 2 hours, gently shaking at room temperature. After three washes with SPOT wash buffer, *Norwalk* virus mAb 3912 (Hale, et al., 2000) was diluted 1:1000 in SPOT wash buffer and incubated with the membrane for one hour, gently shaking at room temperature. The membrane was washed three more times with SPOT wash buffer and then the secondary antibody was diluted 1:5000 and applied to the membrane at room temperature for 45 minutes. SPOTs were developed with SuperSignal West pico chemiluminescent substrate (Thermo Scientific) for 1 minute and then exposed to autoradiography film (Denville Scientific).

Example 2

Identification of Exemplary Peptides that Bind *Norovirus*

Screening a random 12-mer peptide phage library for *Norwalk*-binding peptides.—A commercially available M13 phage display library containing random sequence 12-mer peptides fused to geneIII protein was used for biopanning with immobilized NV-VLP as the target. Five rounds of panning against immobilized NV-VLPs were performed in two independent library panning experiments. After rounds 3-5, 8-12 individual phage clones from each experiment The binding of each phage clone to immobilized NV-VLP was tested by phage ELISA. For these experiments, 0-5 µg of NV-VLP or bovine serum albumin (BSA), as a negative control, was adsorbed onto a 96-well plate and $5 \times 10^{10}$ pfu of phage were added to each well and binding was detected with an HRP-conjugated M13 phage antibody (FIG. 1). The results demonstrated that all three phage clones were able to bind to NV-VLP in a dose-dependent manner and did not bind to BSA. The NV-N-R5-1 clone (Table 1) displayed the highest ELISA signals, while NV-O-R5-6 displayed the weakest signals.

Figure 2:
FIG. 2—NV-VLP binding to SPOT peptide array. NV-VLP-binding peptide sequences, mutant peptides, and unrelated peptides indicated were synthesized on a cellulose membrane by SPOT synthesis (Frank & Overwin, 1996). NV-VLP was incubated with the membrane and binding was detected with NV-VLP mAb 3912 [SEQ ID NOS. 1, 2, 3, 4, 5, 6, 7, 8].

The ability of the peptide encoded in each phage clone to bind NV-VLPs in the absence of the phage was tested using a peptide array. SPOT synthesis was performed to create a peptide array that included each of the candidate peptide sequences, as well as point or deletion mutants that were hypothesized to disrupt binding (Frank & Overwin, 1996). In addition, the array contained T7 and Strep-Tag II peptide sequences, which are unrelated to the phage-encoded peptides, and thereby serve as controls for nonspecific binding. NV-VLP was incubated with the peptide array and binding was detected with mAb 3912, which recognizes NV-VLP (FIG. 2). The data indicated that NV-VLP binds the phage peptides and does not bind the negative control peptides. Therefore, the results demonstrate that the peptides alone, in the absence of the phage context, interact specifically with NV-VLP.

Figure 3:
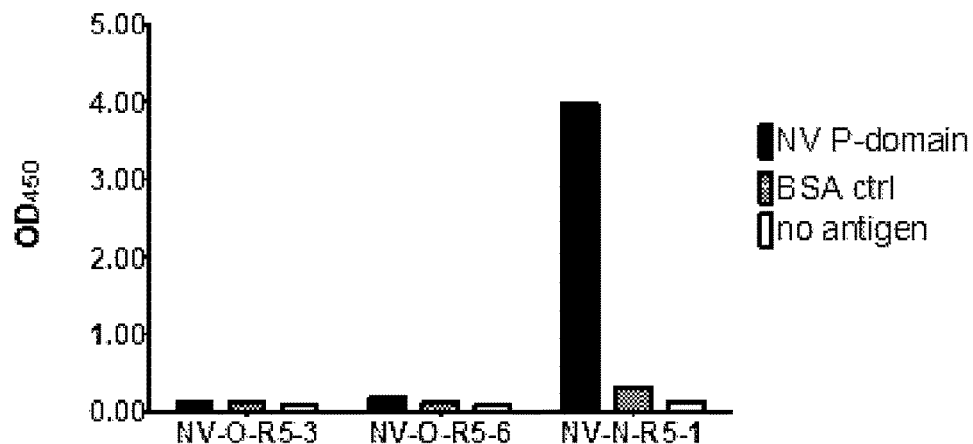
FIG. 3—Phage binding to NV P-domain. 5 µg of NV P-domain, unrelated protein BSA, or no protein, as indicated by the different symbols outlined in the figure insert, was immobilized in microtiter wells. Binding of each phage, indicated on X-axis, was detected with HRP-conjugated M13 phage antibody, followed by determination of the $OD_{450}$ (Y-axis).

Phage binding is specific to the protruding domain of VLP. The major capsid protein of NoV, VP1, is composed of an inner shell domain and an outer protruding domain (P-domain), which is further subdivided into the P1 subdomain and the outermost, surface exposed, P2 subdomain (Prasad, et al., 1999). However, we have previously observed that VLPs adsorbed to a polystyrene surface can have altered structures due to protein unfolding that exposes different epitopes and affects the binding of antibodies (Ajami et al. Manuscript in progress). Phage displaying peptides that bind to the P-domain were desired as they were hypothesized to be most likely to bind to native virus. To test for the possible P-domain binding, purified NV P-domain or BSA as a negative control were adsorbed into the wells of a 96-well plate and each phage was tested for binding as done previously with NV-VLP (FIG. 3). The results revealed that only one phage clone, NV-N-R5-1, was able to bind specifically to the purified NV P-domain. Because the peptide sequences from all three phage clones share a common motif, it is likely that they are binding to the same epitope on NV-VLPs. However, the surrounding sequence likely affects the ability of the phage to bind to the native P-domain structure, which would explain why two phages were able to bind to VLPs adsorbed to the plate surface, but not properly folded P-domain.

Figure 4:
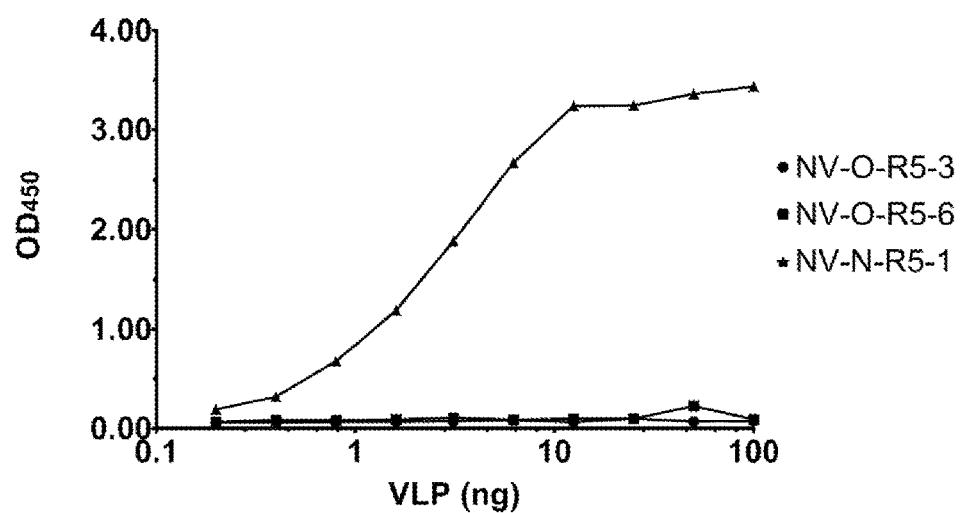
FIG. 4—Phage binding to captured NV-VLP. 0-100 ng of NV-VLP was captured by immobilized NV polyclonal antibody. Binding of each phage, indicated in the figure legend, was detected by horseradish peroxidase (HRP)-conjugated M13 phage antibody, followed by determination of the $OD_{450}$ (Y-axis).

Because the NV-N-R5-1 clone was the only phage to bind to purified P-domain by ELISA, it was considered that the NV-N-R5-1 clone would also be the only phage that displayed binding to antibody-captured VLPs, which maintain their original conformation in contrast to VLPs directly adsorbed to the plate surface. Polyclonal anti-NV-VLP antibody was adsorbed into the wells of a 96-well plate and 0-100 ng of NV-VLP was incubated for capture in each well. A total of $1\times10^9$ phage was added, non-binders were washed away, and retained phage were detected with an HRP-conjugated M13-phage antibody (FIG. 4). As expected, NV-N-R5-1 was the only phage that bound to antibody-captured VLPs. Because antibody-captured VLPs morphologically and antigenically mimic native virions, it was considered important that a candidate diagnostic phage clone interact with antibody-captured VLPs. Therefore, the NV-N-R5-1 clone was chosen to test for feasibility of use in detection of NV in clinical stool samples.

Figure 5:
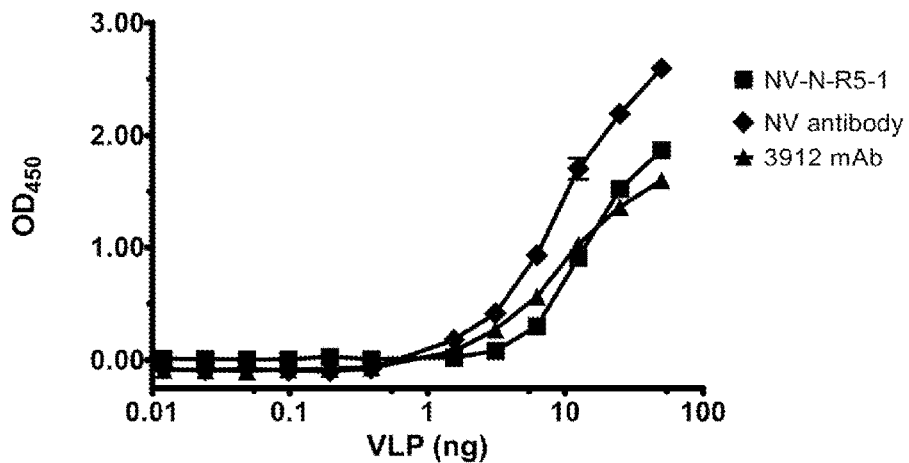
FIG. 5—NV-N-R5-1 phage binding to NV-VLP in NoV-negative stool suspension. 0-10 ng of NV-VLP (X-axis) was diluted in 10% NoV-negative stool suspension and captured by immobilized NV polyclonal antibody. NV-VLP was detected by $1 \times 10^9$ pfu NV-N-R5-1 phage, 1:2500 dilution of NV polyclonal antibody, or a 1:500 dilution of 3912 mAb, as indicated in the figure legend. Binding was detected by M13 antibody or secondary antibody and determination of the $OD_{450}$ (Y-axis).

NV-N-R5-1 sensitivity determined for NV VLP in stool samples.—As a first step towards applying the NV-N-R5-1 phage as a sensor for virus in clinical samples, the sensitivity of detection of the phage was determined. For this purpose, an ELISA experiment was performed under the same conditions as described for the antibody-captured VLP except that NV-VLP was diluted in a 10% clarified solution of NoV-negative stool sample (FIG. 5). The results indicated that NV-N-R5-1 phage is able to interact with NV-VLP under these conditions with similar sensitivity to the diagnostic mAb 3912. Notably, the diverse components of the stool did not inhibit the interaction of the phage with NV-VLPs. These data were further used to determine the lowest limit of detection of NV-N-R5-1 for NV-VLP in a 10% suspension of NoV-negative stool. Using a threshold for specific positive signal of three standard deviations over the [VLP]=0 background, 1.56 ng of NV-VLP was the lowest amount of VLP to show positive signal with detection by NV-N-R5-1 phage. The lowest limit of detection for the polyclonal antibody was also 1.56 ng and the lowest limit of detection for mAb 3912 was 3.13 ng. Therefore the NV-N-R5-1 phage was determined to be slightly more sensitive for NV than the commercially available diagnostic mAb 3912 and on par with a widely characterized polyclonal antibody.

Figure 6:
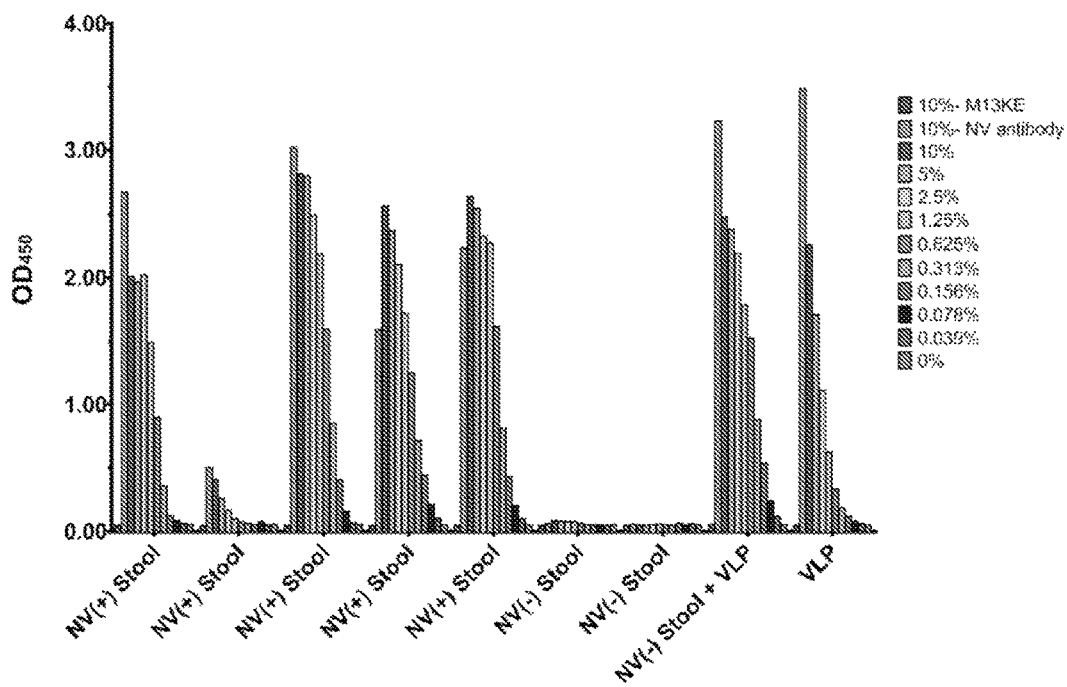
FIG. 6—NV-N-R5-1 phage detection of NoV in stool suspensions from infected volunteers. Stool samples were collected from persons with and without NV infection. NV-positive, NoV-negative, or 100 ng of NV-VLP in NoV-negative stool or buffer (X-axis) was serially diluted to concentrations indicated on the figure legend and was then captured by immobilized NV polyclonal antibody. Binding was detected by M13 control phage, NV polyclonal antibody, or NV-N-R5-1 phage ($OD_{450}$ indicated on Y-axis).

NV-N-R5-1 phage is able to detect *norovirus* in clinical stool samples.—Based on the above comparisons of the sensitivity of the NV-N-R5-1 phage with the mAb 3912, it was hypothesized that the phage would be effective at detecting virus from clinical samples. This was tested by using the anti-NV polyclonal antibody to capture virus from NV-positive stool samples and then using NV-N-R5-1 phage to detect the presence of virus (FIG. 6). The results showed that NV-N-R5-1 phage was able to detect NV in all of the NV-positive stool suspensions with similar signal to the NV polyclonal antibody and no signal was observed in the previously characterized NoV-negative samples. These results demonstrate that the NV-N-R5-1 phage is able to interact with native NV in a specific manner and is not inhibited by any of the components of the stool suspension.

REFERENCES

Ambert-balay & Pothier, *J Clin Virol.* 56(3):194-8, 2013.
Atmar & Estes, *Clin Microbiol Rev.* 14(1):15-37, 2001.
Atmar, *Emerg Infect Dis.* 14(10):1553-1557, 2008.
Bok & Green, *N Engl J Med.* 367:2126-2132, 2012.
Fankhauser, et al., *J Infect Dis.* 178:1571-1578, 1998.
Frank & Overwin, *Methods Mol Biol.* 66:149-169, 1996.
Glass, et al., *N Engl J Med* 361:1776-1785, 2009.
Hale, et al., *Clin Diagn Lab Immunol.* 6:142-145, 1999.
Hale, et al., *J Clin Microbiol.* 38:1656-1660, 2000.
Hoffmann, et al., *J Food Prot.* 75:1292-1302, 2012.
Hutson, et al., *Trends Microbiol.* 12:279-287, 2004.
Johnston, et al., *Clin Infect Dis.* 45:534-540, 2007.
Kaufmann, et al., *J Pediatr Gastroenterol and Nutr.* 40:328-333, 2005.
Kirby, et al., *J Clin Virol.* 49:254-257, 2010.
Kroneman, et al., *J Clin Virol.* 51:121-125, 2011.
Lopman, et al., *Emerg Infect Dis.* 10:1827-1834, 2004.
Monjezi, et al., *J Virol Methods.* 187(1):121-6, 2013.
Parker, et al., *J Virol.* 79:7402-7409, 2005.
Paschke, *Appl Microbiol Biotechnol.* 70:2-11, 2006.
Prasad, et al., *Science.* 286:287-290, 1999.
Rakonjac, et al., *Curr Issues Mol Biol.* 13:51-76, 2011.
Samoylova, et al., *J Virol Methods.* 183:63-68, 2012.
Scallan, et al., *Emerg Infect Dis.* 17:7-15, 2011.
Schofield, et al., *Bacteriophage.* 2:105-283, 2012.
Sidhu, et al., *Chembiochem.* 4:14-25, 2003.
Stratmann, et al., *J Clin Microbiol.* 40:4244-4250, 2002.
Trivedi, et al., *JAMA.* 308:1668-1675, 2012.
Zheng, et al., *Virology.* 346:312-323, 2006.

What is claimed is:

1. A composition comprising one or both of: a peptide comprising the sequence of SEQ ID NO: 1, SEQ ID NO: 3, SEQ ID NO: 5, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, or SEQ ID NO: 23; and a phage that encodes the peptide.

2. The composition of claim 1, wherein the peptide is no more than about 50 amino acids in length.

3. The composition of claim 1, wherein the peptide is labeled.

4. The composition of claim 3, wherein the label is fluorescent, radioactive, or colored.

5. A kit comprising the composition of claim 1.

* * * * *